United States Patent
Suzuki et al.

(10) Patent No.: US 6,355,585 B1
(45) Date of Patent: Mar. 12, 2002

(54) GLASS POWDER FOR GLASS IONOMER CEMENT

(75) Inventors: Yoshimasa Suzuki; Masaaki Kaneko; Kaori Okada; Kazuo Hirota, all of Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/516,204

(22) Filed: Feb. 29, 2000

(30) Foreign Application Priority Data

Mar. 10, 1999 (JP) .......................................... 11-063427

(51) Int. Cl.[7] .......................... A61K 6/06; C03C 3/062; C03C 12/00; C03C 17/28
(52) U.S. Cl. ........................... 501/35; 106/35; 523/116; 433/226; 433/228.1
(58) Field of Search .............................. 106/35; 501/35, 501/73; 523/116; 433/226, 228.1

(56) References Cited

U.S. PATENT DOCUMENTS

| 4,250,277 A | * | 2/1981 | Maries et al. ................. 106/35 |
|---|---|---|---|
| 4,775,592 A | | 10/1988 | Akahane et al. ............... 501/57 |
| 4,900,697 A | | 2/1990 | Akahane et al. ............ 428/406 |
| 5,063,257 A | * | 11/1991 | Akhane et al. ............. 523/116 |
| 6,264,472 B1 | * | 7/2001 | Okada et al. ............ 433/228.1 |

\* cited by examiner

*Primary Examiner*—C. Melissa Koslow
(74) *Attorney, Agent, or Firm*—Oblon, Spivak, McClelland, Maier & Neustadt, P.C.

(57) ABSTRACT

A glass powder for glass ionomer cement is disclosed, containing a glass powder for glass ionomer cement having a shape in which a major axis length is from 3 to 1,000 times a minor axis length, in a glass powder for glass ionomer cement. The glass powder for glass ionomer cement having a shape in which a major axis length is from 3 to 1,000 times a minor axis length is a fibrous glass having a minor axis length of from 0.1 to 100 $\mu$m and a major axis length of 500 $\mu$m or less, and its content is within a range of from 0.1 to 80% by weight, being enable to provide a glass ionomer cement set material having a high mechanical strength, particularly bending strength and tensile strength.

5 Claims, No Drawings

GLASS POWDER FOR GLASS IONOMER CEMENT

BACKGROUND OF THE INVENTION

1. Field of the Invention

The present invention relates to a glass powder for glass ionomer cement that is used in the medicine, and preferably in the dentistry. More particularly, the invention relates to a glass powder for glass ionomer cement having an effect for improving physical properties of glass ionomer cement, as compared with the related art glass powders for glass ionomer cement.

2. Description of the Related Art

Glass ionomer cements are used by reacting an acid made of, as the main component, an acid such as polycarboxylic acids with a glass powder for glass ionomer cement in the presence of water. The glass ionomer cements have superior characteristics such that they are extremely good in biocompatibility, translucent and superior in esthetics, have a superior adhesive force to tooth structure such as enamels and dentins, and have a caries-preventive function owing to fluoride contained in the glass powder for glass ionomer cement. For these reasons, the glass ionomer cements are a material widely used in the dentistry for filling of a caries cavity, cementing of a crown, inlay and bridge or an orthodontic band, lining of a cavity, a sealer for filling a root canal, core construction, pit and fissure sealant, and the like.

Furthermore, at present, resin-reinforced type glass ionomer cements have been developed which comprise a glass ionomer cement having a polymerizable resin component added thereto in order to prevent brittleness due to a water content during initial setting, which has hitherto been said to be a disadvantage of the glass ionomer cements, improve physical properties such as mechanical strengths and adhesion to a tooth structure, and have a superior adhesion to dental metals, resins, porcelains, etc. Moreover, glass ionomer cements in which a photopolymerization catalyst is used as a catalyst for polymerizing the polymerizable resin component and which are rapidly set by visible light are also developed, whereby more applications are expanded.

However, the glass ionomer cements are low in mechanical strengths such as bending strength and tensile strength, as compared with resin-based cements and the like. And, when a stress is applied, the glass ionomer cements have a drawback that they are readily broken due to fine voids or defects in an interior of a cement set material, cracks on a surface of the set material, and the like. This is considered to be caused by the fact that, since a matrix portion constituted by reacting a polycarboxylic acid, water, and a glass surface portion is brittle as compared with a glass portion constituted via a firm covalent bond of Si—O or Al—O and having a three-dimensional net-work structure, when a stress is concentrated into fine cracks generated in part of the set material, the cracks evade the glass portion having high strengths and are rapidly expanded in the matrix portion having low strengths, whereby the set material is broken.

For these reasons, in the dentistry, the glass ionomer cements cannot be applied for filling a cavity to which a relatively large load is applied, such as a class II cavity or a class IV cavity. Also, where the glass ionomer cements are used as a cement for bone, they have been considered to be insufficient in mechanical strengths as compared with the resin-based cements.

SUMMARY OF THE INVENTION

This invention is aimed to overcome the drawbacks of the glass ionomer cements as described above and to provide a glass powder for glass ionomer cement capable of obtaining glass ionomer cements having high mechanical strengths, particularly bending strength and tensile strength.

In order to achieve the above-described aim, the present inventors made extensive and intensive investigations on a glass powder to be used for glass ionomer cement. As a result, they paid attention to the fact that, in the related art glass powders for glass ionomer cement, after a glass raw material has been melted and cooled, the resulting product is crashed into a powdered having a mean particle size of from 0.02 $\mu$m to 30 $\mu$m over from several hours to several tens hours by means of a mill, whereby a shape having a major axis length and a minor axis length substantially equal to each other is obtained in a long-term processing by the mill. And, finally, it has been found that, when such the related art glass powder for glass ionomer cement is compounded with a glass powder for glass ionomer cement having a shape in which a major axis length is from 3 to 1,000 times a minor axis length, a reinforcing function in the fibrous fillers, a high effect of which is already confirmed in the field of engineering plastics, etc., is combined with a nature which the glass for glass ionomer cement having such a specific shape possesses to be reactive with an acid component, the matrix portion is reinforced, and the mechanical strengths of the glass ionomer cement set material, such as bending strength and tensile strength, can be markedly improved, leading to accomplishment of this invention.

Specifically, the present invention relates to a glass powder for glass ionomer cement comprising a glass powder for glass ionomer cement having a shape in which a major axis length is from 3 to 1,000 times a minor axis length, contained in a glass powder for glass ionomer cement. When the glass powder for glass ionomer cement according to the present invention is used, it has become possible to markedly improve the mechanical strengths, in addition to the characteristics of the related art glass powders for glass ionomer cement including the biocompatibility, the esthetics, the adhesion to a tooth structure, and the caries-preventive function.

DETAILED DESCRIPTION OF THE INVENTION

In the present invention, with respect to the shape of powder particles, at least 200 particles are arbitrarily selected, and when a projected image of each of the powder particles on a planar surface is sandwiched by two parallel lines, an average of distances at which a gap between the two parallel lines becomes minimum is expressed as a minor axis length, whereas, when the particle is sandwiched by two parallel lines in the perpendicular directions to the former two parallel lines, an average of gaps between the latter parallel lines is expressed as a major axis length.

In the present invention, with respect to the glass powder for glass ionomer cement having a shape in which a major axis length is from 3 to 1,000 times a minor axis length, when the major axis length is less than 3 times the minor axis length, a function enough for suppressing cracks that advance in the matrix portion cannot be obtained. On the other hand, when the major axis length exceeds 1,000 times the minor axis length, the surface smoothness after hardening is inferior, and the mechanical strengths are lowered. Particularly, it is preferred that the major axis length is from 5 to 200 times the minor axis length.

As the glass powder for glass ionomer cement having a shape in which a major axis length is from 3 to 1,000 times a minor axis length, which is used in the present invention, are preferred fibrous ones having a minor axis length of from 0.1 to 100 μm and a major axis length of 500 μm or less. When the minor axis length is less than 0.1 μm, the effect for improving the mechanical strengths of the glass ionomer cement set material is low, and, when it exceeds 100 μm, the surface area of the glass powder that reacts with the acid becomes small, and the reactivity is lowered, whereby the physical properties of the glass ionomer cement set material are not improved at all but are liable to be lowered. On the other hand, when the major axis length exceeds 500 μm, it is difficult to obtain mixtures exhibiting a sufficient fluidity during mixing and using with the related art glass powder for glass ionomer cement, and the operability tends to be lowered. In particular, in the case of use in the dentistry, the surface smoothness becomes worse, whereby the esthetics tend to be inferior. It is particularly preferred that the minor axis length is from 0.5 to 50 μm, and the major axis length is from 3 to 200 μm.

When the glass powder for glass ionomer cement having a shape in which a major axis length is from 3 to 1,000 times a minor axis length is contained in the related art glass powder for glass ionomer cement, it is preferred that the amount of the glass powder according to the present invention is within the range of from 0.1 to 80% by weight based on the total weight of the glass powders. When the amount of the glass powder according to the present invention is less than 0.1% by weight based on the total weight of the glass powders, the reinforcing effect to the set material is hardly obtained. On the other hand, when it exceeds 80% by weight, the operability is lowered, and the strengths tend to be lowered. Most suitably, the amount of the set glass powder according to the present invention is within the range of from 1 to 50% by weight based on the total weight of the glass powders.

As described above, since the glass powder for glass ionomer cement having a shape in which a major axis length is from 3 to 1,000 times a minor axis length has a reinforcing effect to the cement set material owing to its shape, and in addition, owing to a nature which the glass for glass ionomer cement is reactive with the acid component, it has an effect to more ensure the reinforcing effect to the cement set material, as compared with the case in which generally used fibrous fillers that are not reactive with the matrix are added. Such effect can be attained by a composition upon which an acid-base reaction thoroughly occurs during mixing with the glass powder component for glass ionomer cement having a shape in which a major axis length is from 3 to 1,000 times a minor axis length with an acid such as polycarboxylic acids, in the presence of water, like the related art glass powders for glass ionomer cement. However, it is not necessary that the glass powder component for glass ionomer cement having a shape in which a major axis length is from 3 to 1,000 times a minor axis length, which is used in the present invention, should be equal to the composition and compounding amount of the original glass powder for glass ionomer cement to be compounded.

The glass powder for glass ionomer cement having a shape in which a major axis length is from 3 to 1,000 times a minor axis length is a glass powder comprising silica and alumina as the major components, and specifically, includes glass powders for glass ionomer cement comprising silica and alumina as the major components and having calcium fluoride, aluminum fluoride, aluminum phosphate, or the like mixed therewith, as disclosed in Japanese Patent Laid-Open Nos. 63-201038, equivalent to U.S. Pat. No. 4,900,679, and 62-067008, equivalent to U.S. Pat. No. 4,775,592.

Of these glass powders for glass ionomer cement is particularly preferred a dental fluoroaluminosilicate glass powder containing, as its components, from 10 to 21% by weight of Al, from 9 to 21% by weight of Si, and from 1 to 20% by weight of F, and further at least one of Sr, Ca and La in the total amount of from 10 to 34% by weight. Besides, as the glass powder for glass ionomer cement having a shape in which a major axis length is from 3 to 1,000 times a minor axis length, any glass powders containing silica and alumina as the major components, which are reactive with an acid, can be used in the present invention. An aluminosilicate glass powder containing silica and alumina as major components and having phosphorus pentoxide, etc. mixed therewith, and the like can also be used.

Needless to say, by using the glass powder for glass ionomer cement containing the glass powder for glass ionomer cement having a shape in which a major axis length is from 3 to 1,000 times a minor axis length according to the present invention, the effect for improving the mechanical strengths of the cement set material is applicable to resin-reinforced type glass ionomer cements having a polymerizable monomer and a chemical polymerization catalyst or a photopolymerization catalyst compounded therewith. Incidentally, if desired, the glass powder for glass ionomer cement according to the present invention can be compounded with a usually used polymerization inhibitor or pigment, etc.

It is preferred that the glass powder for glass ionomer cement having a shape in which a major axis length is from 3 to 1,000 times a minor axis length, which is used in the present invention, is prepared by drawing a molten glass into a fine fibrous state and then crashing the fibers so that the major axis length may not become less than 3 times the minor axis length.

Next, an example of the preparation of the glass powder for glass ionomer cement having a shape in which a major axis length is from 3 to 1,000 times a minor axis length will be now described. That is, the above-described glass raw materials are each weighed and mixed with each other, and the mixture is melted upon heating at from 1,100° C. to 1,500° C. in an appropriate crucible such as a platinum crucible or a ceramic crucible. Thereafter, the molten glass is dropped in a cylindrical rotating body having a numerous number of pores in a side wall thereof, and the glass is made spurt out from the pores by a centrifugal force, whereby the glass becomes fibrous. At this time, though the dimension of the pores in the side wall of the rotating body varies depending on the equilibrium of the structure and the number of revolutions of the rotating body, usually, a fibrous glass having a minor axis length (i.e., a fiber diameter) of from 0.1 μm to 100 μm can be obtained, when using one having a diameter of 8 mm or less. The thus produced fibrous glass is crashed under appropriate conditions by means of a mill, etc., whereby the glass powder for glass ionomer cement having a shape in which a major axis length is from 3 to 1,000 times a minor axis length can be prepared.

In addition to the above-described method, a flame drawing method in which the molten glass is dropped from an orifice to continuously spin fibrous glasses having a diameter of 1 mm or less, and their lower ends are blown out while the fibrous glass being inserted in a high-temperature and high-speed flame, to obtain short fibrous glasses, or a vortex method in which the molten glass is dropped from an orifice, and a plurality of high-temperature and high-pressure gasses are blown in a vortex state to obtain fibrous glasses, is also usable to prepare the glass powder for glass ionomer cement having a shape in which a major axis length is from 3 to 1,000 times a minor axis length.

The glass powder for glass ionomer cement having a shape in which a major axis length is from 3 to 1,000 times a minor axis length, which is used in the present invention, may be subjected to a surface processing with an acid or a fluoride in the same manner as in the related art powders for glass ionomer cement. By the surface processing with an acid or a fluoride, the fluidity of the cement slurry increases, the operability is improved, and these tting reaction can be made sharp. Examples of the acid which can be used for the processing include phosphoric acid, hydrochloric acid, pyrophosphoric acid, tartaric acid, citric acid, glutaric acid, malic acid, and acetic acid. Also, monobasicphosphates and dibasicphosphates as acidic substances are included. In addition, fluorides such as a luminum fluoride, zinc fluoride, tin fluoride, zirconium fluoride, acidic sodium fluoride, and acidic potassium fluoride may be used.

Furthermore, the glass powder for glass ionomer cement having a shape in which a major axis length is from 3 to 1,000 times aminor axis length, which is used in the present invention, may be subjected to a surface processing with an organic compound containing a polymerizable ethylenically unsaturated double bond, and preferably, is subjected preferably to a surface processing with the organic compound containing a polymerizable ethylenically unsaturated double bond in an amount of from 0.01 to 20 parts by weight based on 100 parts by weight of the glass powder for glass ionomer cement. Examples of unsaturated organic compounds containing a polymerizable ethylenically doublebond which can be used for this surface processing include vinyl-based silane coupling agents such as vinyl trimethoxysilane, vinyl triethoxysilane, γmethacryloxylpropyl trimethoxysilane, γ-methacryloxylpropylmethyl dimethoxysilane, vinyl trichlorosilane, and vinyl tris (2-methoxyethoxy) silane; and unsaturated carboxylic acids such as methacrylic acid, acrylic acid, and maleic acid.

Three-point Bending Test

A cement after mixing was filled in an acrylic resin-made tube to obtain a cylindrical set material having a diameter of 3 mm and a length of 25 mm. Incidentally, in the case of a photopolymerization type glass ionomer cement, light irradiation was carried out for 20 seconds by using a light irradiator (a trade name: GC LABOLIGHT LV-II, manufactured by GC Corporation), thereby setting the cement. The thus obtained specimen was immersed in distilled water at 37° C. for 24 hours and then subjected to a three-point bending test at a span of 20 mm and at a cross head speed of 1 mm/min. by means of a universal testing machine (a trade name: Autograph, manufactured by Shimadzu Corporation). The test was carried out for ten specimens.

Diametral Tensile Strength Test

A cement after mixing was filled in a metallic mold to obtain a cylindrical set material having a diameter of 4 mm and a length of 6 mm. Incidentally, in the case of a photopolymerization type glass ionomer cement, light irradiation was carried out for 20 seconds by using a light irradiator (a trade name: GC LABOLIGHT LV-II, manufactured by GC Corporation), thereby setting the cement. The thus obtained specimen was immersed in distilled water at 37° C. for 24 hours and then subjected to a diametral tensile strength test while attaching a tool to a side surface of the cylindrical sample at a cross head speed of 1 mm/min. by means of a universal testing machine (a trade name: Autograph, manufactured by Shimadzu Corporation). The test was carried out for ten specimens.

EXAMPLES 1

Aluminumoxide (19.8 g), 35.8 g of silica, 22.4 g of calcium oxide, 15.1 g of aluminum phosphate, and 6.9 g of strontium fluoride were each weighed and thoroughly mixed in a mortar. A platinum crucible charged with this raw material powder for glass was placed in an electric furnace at room temperature, and the temperature in the electric furnace was elevated to 1,300° C. over about 3 hours, thereby melting the glass. Thereafter, the temperature was kept constant for 2 hours to make the molten glass clear, and then, the glass was taken out from the electric furnace. The molten glass was pored into a rotating vessel previously heated at 1,000° C. and made spurt out from pores having a diameter of 3.1 mm provided in a side wall of the rotating body, topreparea fibrous glass. Thereafter, 300 g of the fibrous glass was crashed in a ball mil for 25 minutes to obtain a glass powder having a minor axis length of 10.5 $\mu$m and a major axis length of 40 $\mu$m.

This glass powder was compounded in an amount of 30% by weight into a commercially available glass powder for glass ionomer cement (a trade name: Fuji I Powder, made by GC Corporation) . This cement powder (1.8 g) was mixed with 1.0 g of a commercially available liquid for glass ionomer cement (a trade name: Fuji I Liquid, made by GC Corporation), followed by subjecting to the tests. As a result, the three-point bending strength and the diametral tensile strength were 36±6 MPa and 20.5±2 MPa, respectively.

EXAMPLE 2

Aluminumoxide (21.0 g), 45.1 g of silica, 12.5 g of calcium fluoride, 10.2 g of aluminum phosphate, and 12.0 g of calcium carbonate were each weighed and thoroughly mixed in a mortar. A platinum crucible charged with this raw material powder for glass was placed in an electric furnace at room temperature, and the temperature in the electric furnace was elevated to 1,100° C. over about 3 hours, thereby melting the glass. Thereafter, the temperature was kept constant for 2 hours to make the molten glass clear, and then, the glass was taken out from the electric furnace. The molten glass was pored into a rotating vessel previously heated at 1,000° C. and made spurt out from pores having a diameter of 1.0 mm provided in a side wall of the rotating body, to prepare a fibrous glass. Thereafter, 300 g of the fibrous glass was crashed in a ball mil for 8 minutes to obtain a glass powder having a minor axis length of 8.0 $\mu$m and a major axis length of 105 $\mu$m.

To 100 g of this glass powder was added 20 g of an ethanol solution containing 5% by weight of γ-methacryloxypropyl trimethoxysilane, and after thoroughly stirring, the mixture was dried at 120° C. for 2 hours by using a vapor dryer. The dried product was compounded in an amount of 48% by weight into a commercially available glass powder of photopolymerization type glass ionomer cement (a trade name: Fuji Lute Powder, made by GC Corporation). This cement powder (2.0 g) was mixed with 1.0 g of a commercially available liquid for photopolymerization type glass ionomer cement (a trade name: Fuji Lute Liquid, made by GC Corporation), followed by subjected to the tests. As a result, the three-point bending strength and the diametral tensile strength were 47±4 MPa and 32.5±2 MPa, respectively.

EXAMPLE 3

A glass powder having a minor axis length of 22.1 $\mu$m and a major axis length of 250 $\mu$m was prepared in the same manner as in Example 1, except that the diameter of the pores in the side wall of the rotating body was changed from 3.1 mm to 7.0 mm and that the revolution rate of the rotating body and the crashing time of the fibrous glass were adjusted. Thereafter, this glass powder was compounded in an amount of 10% by weight into a commercially available glass powder for glass ionomer cement (a trade name: Fuji I Powder, made by GC Corporation), followed by subjecting to the tests in the same manner as in Example 1. As a result, the three-point bending strength and the diametral tensile strength were 38±4 MPa and 25.3±2 MPa, respectively.

EXAMPLE 4

A glass powder having a minor axis length of 2.5 $\mu$m and a major axis length of 183 $\mu$m was prepared in the same manner as in Example 2, except that the diameter of the pores in the side wall of the rotating body was changed from 3.1 mm to 2.2 mm and that the revolution rate of the rotating body and the crashing time of the fibrous glass were adjusted. Thereafter, the surface processing was carried out in the same manner as in Example 2, and the resulting product was compounded in an amount of 1.2% by weight into a commercially available glass powder of photopolymerization type glass ionomer cements (a trade name: Fuji Lute Powder, made by GC Corporation), followed by subjecting to the tests in the same manner as in Example 2. As a result, the three-point bending strength and the diametral tensile strength were 44±6 MPa and 32.1±1 MPa, respectively.

EXAMPLE 5

A glass powder having a minor axis length of 1.3 $\mu$m and a major axis length of 40 $\mu$m was prepared in the same manner as in Example 1, except that the diameter of the pores in the side wall of the rotating body was changed from 3.1 mm to 1.3 mm and that the revolution rate of the rotating body and the crashing time of the fibrous glass were adjusted. Thereafter, this glass powder was compounded in an amount of 18% by weight into a commercially available glass powder for glass ionomer cement (a trade name: HY-BOND Glass Ionomer F Powder, made by Shofu Inc.), and 2.5 g of the resulting glass powder was mixed with 0.1 g of a commercially available liquid for glass ionomer cement (a trade name: HY-BOND Glass Ionomer F Liquid, made by Shofu Inc.), followed by subjecting to each of the tests. As a result, the three-point bending strength and the diametral tensile strength were 35±5 MPa and 15.1±2 MPa, respectively.

EXAMPLE 6

A glass powder having a minor axis length of 7.2 $\mu$m and a major axis length of 309 $\mu$m was prepared in the same manner as in Example 2, except that the diameter of the pores in the side wall of the rotating body was changed from 3.1 mm to 2.8 mm and that the revolution rate of the rotating body and the crashing time of the fibrous glass were adjusted. Thereafter, this glass powder was compounded in an amount of 4.5% by weight into a commercially available glass powder for glass ionomer cement (a trade name: HY-BOND Glass Ionomer F Powder, made by Shofu Inc.) the same as in Example 5, and 2.5 g of the resulting glass powder was mixed with 0.1 g of a commercially available liquid for glass ionomer cement (a trade name: HY-BOND Glass Ionomer F Liquid, made by Shofu Inc.), followed by subjecting to each of the tests. As a result, the three-point bending strength and the diametral tensile strength were 41±5 MPa and 14.8±2 MPa, respectively.

COMPARATIVE EXAMPLE 1

A commercially available glass powder for glass ionomer cement (a trade name: Fuji I Powder, made of GC Corporation) (1.8 g) was mixed with 1.0 g of a commercially available liquid for glass ionomer cement (a trade name: Fuji I Liquid, made by GC Corporation), followed by subjecting to each of the tests. As a result, the three-point bending strength and the diametral tensile strength were 20±2 MPa and 12.0±2 MPa, respectively.

COMPARATIVE EXAMPLE 2

A commercially available glass powder for photopolymerization type glass ionomer cement (a trade name: Fuji Lute Powder, made of GC Corporation) (2.0 g) was mixed with 1.0 g of a commercially available liquid for glass ionomer cement (a trade name: Fuji Lute Liquid, made by GC Corporation), followed by subjecting to each of the tests. As a result, the three-point bending strength and the diametral tensile strength were 27±5 MPa and 24.1±2 MPa, respectively.

COMPARATIVE EXAMPLE 3

A commercially available glass powder for glass ionomer cement (a trade name: HY-BOND Glass Ionomer F Powder, made by Shofu Inc.) (2.5 g) was mixed with 1.0 g a commercially available liquid for glass ionomer cement (a trade name: HY-BOND Glass Ionomer F Liquid, made by Shofu Inc.), followed by subjecting to each of the tests. As a result, the three-point bending strength and the diametral tensile strength were 21±6 MPa and 6.1±2 MPa, respectively.

As described above, in the case where a glass powder for glass ionomer cement containing the glass powder for glass ionomer cement having a shape in which a major axis length is from 3 to 1,000 times a minor axis length according to the present invention is used, the strengths, particularly a three-point bending strength and a diametral tensile strength, of the glass ionomer cement set material are improved, as compared with the case where the related art glass powder for dental glass ionomer cement, so that it becomes possible to apply a glass ionomer cement for filling a cavity, etc., which has hitherto been considered to be insufficient in the dentistry. Thus, the present invention greatly contributes to the medical field and is very valuable.

While the present invention has been described in detail and with reference to specific embodiments thereof, it will be apparent to one skilled in the art that various changes and modifications can be made therein without departing from the spirit and scope thereof.

What is claimed is:

1. A glass powder composition suitable for glass ionomer cement comprising from 0.1 to 80% by weight of a glass powder having a shape in which a major axis length is from 3 to 1,000 times a minor axis length.

2. The glass powder composition as claimed in claim 1, wherein the glass powder is a fibrous glass having a minor axis length of from 0.1 to 100 $\mu$m and a major axis length of 500 $\mu$m or less.

3. The glass powder composition as claimed in claim 1, wherein the content of said glass powder is from 1 to 50% by weight.

4. The glass powder composition as claimed in claim 1, wherein said glass powder contains silica and alumina as major components, and which glass powder is reactive with an acid.

5. The glass powder composition as claimed in claim 1, wherein said glass powder is a dental fluoroaluminosilicate glass powder containing, as its major components, from 10 to 21% by weight of Al, from 9 to 21% by weight of Si, and from 1 to 20% by weight of F, and further at least one of Sr, Ca and La in a total amount of from 10 to 34% by weight.

* * * * *